(12) United States Patent
Kleemann et al.

(10) Patent No.: US 6,730,697 B2
(45) Date of Patent: May 4, 2004

(54) DIHYDROTHIAPHENANTHRENECARBON-YLGUANIDINES: COMPOSITION, PROCESS OF MAKING, AND USE AS MEDICAMENT OR DIAGNOSTIC AID

(75) Inventors: Heinz-Werner Kleemann, Bischofsheim (DE); Peter Below, Frankfurt (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 10/350,520

(22) Filed: Jan. 23, 2003

(65) Prior Publication Data

US 2003/0181511 A1 Sep. 25, 2003

Related U.S. Application Data

(60) Provisional application No. 60/360,330, filed on Feb. 27, 2002.

(30) Foreign Application Priority Data

Feb. 7, 2002 (DE) .......................... 102 04 989

(51) Int. Cl.$^7$ .................. A61K 31/38; C07D 327/06
(52) U.S. Cl. .................. 514/432; 514/437; 549/15; 549/16
(58) Field of Search ................ 514/437, 432; 549/16, 15

(56) References Cited

U.S. PATENT DOCUMENTS

| | | | | |
|---|---|---|---|---|
| 4,024,272 A | * | 5/1977 | Rogalski et al. | 514/432 |
| 4,091,108 A | * | 5/1978 | Batchelor et al. | 514/436 |
| 5,604,228 A | * | 2/1997 | Keana et al. | 514/252.11 |
| 6,028,069 A | * | 2/2000 | Baumgarth et al. | 514/227.5 |
| 6,353,018 B1 | * | 3/2002 | Jeppesen et al. | 514/437 |
| 6,384,045 B1 | * | 5/2002 | Hua et al. | 514/291 |

FOREIGN PATENT DOCUMENTS

GB    2171996    9/1986

OTHER PUBLICATIONS

Baumgarth, Manfred et al., (2–Methyl–5–(methylsulfonyl)benzoyl)guanidine Na+/H+ Antiporter Inhibitors, J. Med. Chem., 1997, 40, pp. 2017–2034.

Diederich, Francois et al., Metal–catalyzed Cross–coupling Reactions, Wiley VCH, Weinheim, Germany, 517, 1998.

Giroux, Andre et al., One Pot Biaryl Synthesis via in situ Boronate Formation, Tetrahedron Letters, 1997, 38 (22), pp. 3841–3844.

March, J., Aliphatic Nucleophilic Substitution, Advanced Organic Chemistry, Third Edition, (John Wiley & Sons), 1985, S. 350.

Miyaura, Norio et al., Palladium–Catalyzed Cross–Coupling Reactions of Organoboron Compounds, Chem Review, 1995, 95, (7), pp. 2457–2483.

Staab, H. A., New Methods of Preparative Organic Chemistry IV. Syntheses Using Heterocyclic Amides ( Azolides), Agnew Chem. Int. Ed. English, 1962, 1, (7), pp. 351–367.

Stanforth, Stephen P., Catalytic Cross–coupling Reactions in Biaryl Synthesis, Tetrahedron, 54, (3/3), 1998, pp. 263–303.

Konig W. et al., Perchloric Acid in Peptide Chemistry, Peptides, (1990), Proc. European Peptide Symp., 21st (1991), pp. 143–145.

Miura K. et al. Liquid Crystal Compositions, Chemical Abstracts, vol. 105, No. 74, 1986, p. 653.

\* cited by examiner

*Primary Examiner*—Deborah C. Lambkin
(74) *Attorney, Agent, or Firm*—George G. Wang

(57) ABSTRACT

Dihydrothiaphenanthrenecarbonylguanidine compound of formula I

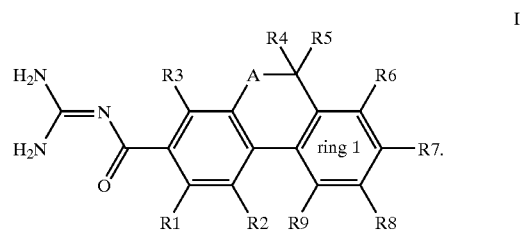

These compounds are potentially suitable as antiarrythmic medicaments with a cardioprotective component for prophylaxis of an infarction and treatment of infarction, and for treatment of angina pectoris. They may also inhibit in a preventive manner the pathophysiological processes involved in the development of ischemia-induced damage, especially in the initiation of ischemia-induced cardiac arrhythmias.

16 Claims, No Drawings

DIHYDROTHIAPHENANTHRENECARBON-YLGUANIDINES: COMPOSITION, PROCESS OF MAKING, AND USE AS MEDICAMENT OR DIAGNOSTIC AID

This application claims the benefit of U.S. Provisional Application No. 60/360,330, filed on Feb. 27, 2002, and German Application No. 10204989.0, filed on Feb. 7, 2002.

SUMMARY OF THE INVENTION

The Scope of Composition

This invention relates to dihydrothiaphenanthrenecarbonylguanidines of formula I, encompassing their composition, process of making, and use as medicament or diagnostic aid.

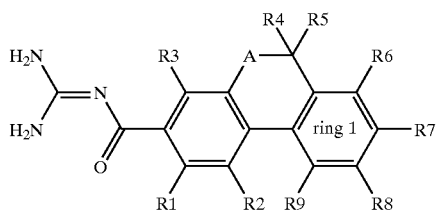

I wherein,

R1 and R3 are independently selected from the group consisting of hydrogen, —(C1–C4)-alkyl, —(C1–C4)-alkoxy, —F, —Cl, —Br, —I, —CN, —NR10R11, —$O_p$—$(CH_2)_n$—$(CF_2)_x$—$CF_3$, and —$(SO_m)_p$—$(CH_2)_n$—$(CF_2)_x$—$CF_3$, wherein:
  R10 and R11 are independently selected from the group consisting of hydrogen, —(C1–C4)-alkyl and —$(CH_2)_n$—$(CF_2)_x$—$CF_3$,
  m=0, 1 or 2,
  n=0, 1, 2, 3, 4, 5 or 6,
  x=0 or 1, and
  p=0 or 1;

R2 is selected from the group consisting of hydrogen, —F, —Cl, —Br, —I, —CN, —(C1–C4)-alkyl, methoxy, and —(C3–C8)-cycloalkyl;

R4 and R5 are independently selected from the group consisting of hydrogen and —(C1–C4) alkyl;

R6, R7, R8 and R9 are independently selected from the group consisting of hydrogen, —(C1–C4)-alkyl; —(C1–C4)-alkoxy, —F, —Cl, —Br, —I, —CN, —NR12R13, —$O_q$—$(CH_2)_r$—$(CF_2)_s$—$CF_3$ and —$(SO_w)_t$—$(CH_2)_u$—$(CF_2)_v$—$CF_3$, wherein:
  R12 and R13 are independently selected from the group consisting of hydrogen and —(C1–C4)-alkyl,
  w=0, 1 or 2,
  r=0, 1, 2, 3, 4, 5, or 6,
  u=0, 1, 2, 3, 4, 5, or 6,
  q=0 or 1
  s=0 or 1
  t=0 or 1, and
  v=0 or 1; or R6 and R7, together with ring 1, form a naphthalene system and R8 and R9 remain as defined above; or R7 and R8, together with ring 1, form a naphthalene system and R6 and R9 remain as defined above; or R8 and R9, together with ring 1, form a naphthalene system and R6 and R7 remain as defined above; and A is selected from the group consisting of —S—, —SO— and —$SO_2$—.

Preference is given to compounds of formula I wherein,

R1 and R3 are independently selected from the group consisting of hydrogen, methyl, ethyl, methoxy, ethoxy, —F, —Cl, —CN, —NR10OR11, —$O_p$—$(CH_2)_n$—$CF_3$ and —$(SO_m)_p$—$(CH_2)_n$—$CF_3$, wherein:
  R10 and R11 are independently selected from the group consisting of hydrogen, methyl, ethyl and —$CH_2$—$CF_3$,
  m=0, 1 or 2,
  n=0, 1, 2 or 3, and
  p=0 or 1;

R2 is selected from the group consisting of hydrogen, —F, —Cl, —CN, —(C1–C4)-alkyl, methoxy, and —(C3–C6)-cycloalkyl;

R4 and R5 are independently selected from the group consisting of hydrogen, methyl and ethyl;

R6, R7, R8 and R9 are independently selected from the group consisting of hydrogen, —(C1–C4)-alkyl, methoxy, ethoxy, —F, —Cl, —CN, —NR12R13, —$O_q$—$(CH_2)_r$—$CF_3$ and —$(SO_w)_t$—$(CH_2)_u$—$CF_3$, wherein:
  R12 and R13 are independently selected from the group consisting of hydrogen, methyl and ethyl,
  w=0, 1 or 2;
  r=0, 1, 2, or 3,
  u=0, 1, 2, or 3,
  q=0 or 1, and
  t=0 or 1; or R6 and R7, together with ring 1, form a naphthalene system and R8 and R9 remain as defined in the preceding section of this claim; or R7 and R8, together with ring 1, form a naphthalene system and R6 and R9 remain as defined in the preceding section; or R8 and R9, together with ring 1, form a naphthalene system and R6 and R7 remain as defined in the preceding section; and A is selected from the group consisting of —S—, —SO— and —$SO_2$—.

Particular preference is given to compounds of formula I, wherein:

R1 is selected from the group consisting of hydrogen, methyl, ethyl, methoxy, ethoxy, —F, —Cl, —NR10R11, —$O_p$—$(CH_2)_n$—$CF_3$ and —$(SO_m)_p$—$(CH_2)_n$—$CF_3$, wherein R10 and R11 are independently selected from the group consisting of hydrogen, methyl, ethyl and —$CH_2$—$CF_3$;

m=0, 1 or 2; n=0 or 1; p=0 or 1;

R2 is selected from the group consisting of hydrogen, —F, —Cl, methyl, and —(C3–C6)-cycloalkyl;

R3, R4 and R5 are hydrogen;

R6, R7, R8 and R9 are independently selected from the group consisting of hydrogen, methyl, methoxy, ethoxy, —F, —Cl, —NR(12)R(13), —$O_q$—$(CH_2)_r$—$CF_3$ and —$(SO_w)_t$—$(CH_2)_u$—$CF_3$, wherein R12 and R13 are independently selected from the group consisting of hydrogen, methyl or ethyl; w=0, 1 or 2; q, r, t and u are independently zero or one; or R6 and R7, together with ring 1, form a naphthalene system and R8 and R9 remain as defined in the preceding section; or R7 and R8, together with ring 1, form a naphthalene system and R6 and R9 remain as defined in the preceding section; or R8 and R9, together with ring 1, form a naphthalene system and R6 and R7 remain as defined in the preceding section; and A is selected from the group consisting of —S—, —SO— and —SO$_2$—.

Further particular preference is given to compounds of formula I, wherein:

R1 is selected from the group consisting of hydrogen, methyl, methoxy, ethoxy, —Cl, —NR10R11, —O—CH$_2$—CF$_3$ and —(SO$_m$)$_p$—(CH$_2$)$_n$—CF$_3$, wherein R(10) and R(11) are independently selected from the group consisting hydrogen, methyl, ethyl and —CH$_2$-CF$_3$; m is 0, 1 or 2; p is 0 or 1;

R2 is selected from the group consisting of hydrogen, —F, —Cl and methyl;

R3, R4 and R5 are hydrogen;

R6, R7, R8 and R9 are independently selected from the group consisting of hydrogen, methyl; methoxy, ethoxy, —F, —Cl, —O—CH$_2$—CF$_3$ and —(SO$_w$)$_t$—(CH$_2$)$_u$—CF$_3$, wherein w is 0, 1 or 2; t and u are independently zero or one; or R6 and R7, together with ring 1, form a naphthalene system and R8 and R9 remain as defined in the preceding section; or R7 and R8, together with ring 1, form a naphthalene system and R6 and R9 remain as defined in the preceding section; or R8 and R9, together with ring 1, form a naphthalene system and R6 and R7 remain as defined in the preceding section; and A is —SO$_2$—.

The present invention further encompasses any pharmaceutically suitable salts of the compounds of formula I.

It is also understood that compounds of formula I may, with appropriate substitution, exist in stereoisomeric forms. If the compounds of formula I contain one or more centers of asymmetry, these may have, independently of one another, the S configuration or the R configuration. All possible stereoisomers, e.g. enantiomers or diastereomers, and mixtures of two or more stereoisomeric forms, e.g. enantiomers and/or diastereomers, in any ratios, are contemplated in the present invention. For example, enantiomers are contemplated in the invention in enantiopure form, both as levorotatory and as dextrorotatory antipodes, and in the form of mixtures of the two enantiomers in various ratios or in the form of racemates. Individual stereoisomers can be prepared if desired by fractionation of a mixture by conventional methods or, for example, by stereoselective synthesis. If mobile hydrogen atoms are present, the present invention also encompasses all tautomeric forms of the compounds of formula I.

The term "—(C1–C4)-alkyl" is understood as meaning an alkyl that contains from 1 to 4 carbon atoms and may be straight-chain or branched, for example, methyl, ethyl, propyl, isopropyl, butyl or tertiary butyl. "—(C3–C8)-cycloalkyl" is understood as meaning a cycloalkyl that contains a 3 to 8-membered ring. Similarly, "—(C3–C6)-cycloalkyl" means a cycloalkyl having a 3 to 6-membered ring. "a naphthalene system" means a chemical group of a substituted or unsubstituted naphthalene ring.

Methods Of Preparing Compounds of Formula I

The invention further relates to a process for preparing compound I, which comprises reacting a compound of formula II

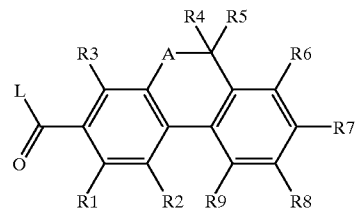

in which R1 to R9 and A are as defined above, and L is a leaving group amenable to easy nucleophilic substitution, with guanidine.

The activated acid derivatives of formula II in which L is an alkoxy group (preferably a methoxy), a phenoxy group, a phenylthio group, a methylthio group, a 2-pyridylthio group, or a nitrogen heterocycle group (preferably 1-imidazolyl), are advantageously obtained in a manner known to those skilled in the art from the underlying carbonyl chlorides (formula II, L=Cl), which in turn can be prepared in a manner known to those skilled in the art from the underlying carboxylic acids (formula II, L=OH), for example with thionyl chloride.

Besides the carbonyl chlorides of formula II (L=Cl), it is also possible to prepare other activated acid derivatives of formula II in a manner known to those skilled in the art directly from the underlying benzoic acid derivatives (formula II, L=OH), such as the methyl esters of formula II with L=OCH$_3$ by treatment with gaseous HCl in methanol, the imidazolides of formula II by treatment with carbonyldiimidazole [L=1-imidazolyl, Staab, Angew. Chem. Int. Ed. Engl. 1, 351–367 (1962)], the mixed anhydrides II with Cl—COOC$_2$H$_5$ or tosyl chloride in the presence of triethylamine in an inert solvent, as well as activations of benzoic acids with dicyclohexylcarbodiimide (DCC) or with O-[(cyano(ethoxycarbonyl)methylene)amino]-1,1,3,3-tetramethyluronium tetrafluoroborate ("TOTU") [Proceedings of the 21st European Peptide Symposium, Peptides 1990, Editors E. Giralt and D. Andreu, Escom, Leiden, 1991]. A number of suitable methods for preparing activated carboxylic acid derivatives of formula II are indicated in J. March, Advanced Organic Chemistry, 3rd Edition (John Wiley & Sons, 1985), page 350, indicating the source literature.

Reaction of an activated carboxylic acid derivative of formula II with guanidine takes place in a manner known to those skilled in the art in a protic or aprotic polar but inert organic solvent. Those which have proved suitable in the reaction of the methyl benzoates (II, L=OMe) with guanidinomethanol, isopropanol or THF from 20° C. to the boiling point of these solvents. Most of the reactions of compounds II with salt-free guanidine have advantageously been carried out in aprotic inert solvents such as THF, dimethoxyethane, dioxane. However, water can also be used as solvent in the reaction of II with guanidine if a base such as, for example, NaOH is employed.

When L is Cl, it is advantageous to add an acid scavenger, e.g. in the form of excess guanidine to bind the hydrohalic acid.

Assembly of the dihydrothiaphenanthrenecarboxylic acid framework advantageously starts from appropriately substituted benzylsulfanyls, phenylmethanesulfinyls or phenylmethanesulfonyls. These are subjected to an intramolecular aryl-aryl coupling as known in principle (see Chem. Rev. 95 (7), 2457 (1995) or "Metal-catalyzed Cross-coupling Reactions", Diederich, Francois; Stang, Peter J.; Editors Germany (1998) Publisher: (Wiley-VCH, Weinheim, Germany), 517) or Tetrahedron (1998), 54(3/4), 263). Coupling of a boronic acid with a suitable aryl halide such as an aryl chloride, aryl bromide, aryl iodide or with a suitable aryl ester such as an aryl mesylate or aryl trifluoromethanesulfonate is preferred. In these cases, the boronic acid function may have been introduced both on the benzyl and on the benzoic acid reactant. It is also particularly preferred to use bistpinakolato)diboron as described in Tetrahedron Lett. (1997), 38(22), 3841–3844. Formula III describes such a starting material in which R(1) to R(9) and A and L have the stated meaning, and X and Y are each a halogen or an —O—SO$_2$CH$_3$ or an —O—SO$_2$CF$_3$. The preferred catalytic metal is palladium, particularly preferably in its complex Pd(dppf)$_2$. The reaction is carried out in a dipolar aprotic solvent, preferably DMF or DMA, at a temperature between 0° C. and the boiling point of the solvent, preferably at temperatures between 40° C. and 120° C.

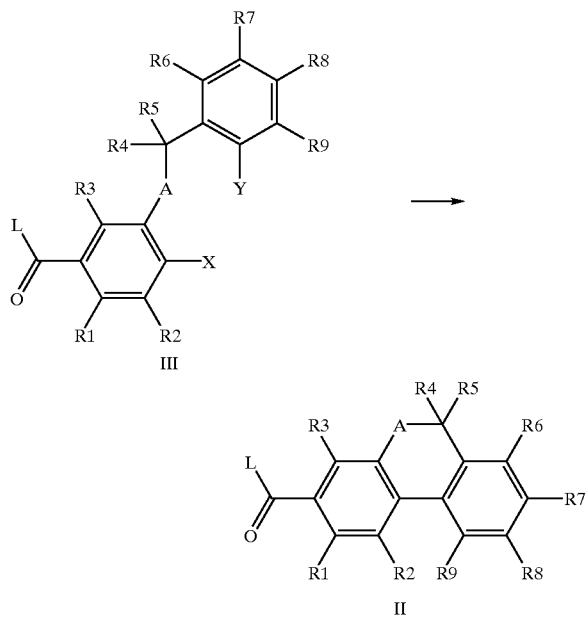

The derivatives of the general formula III are preferably prepared from 3-mercaptobenzoic acid derivatives or from 3-sulfinobenzoic acid derivatives of formula IV with activated benzyl derivatives of formula V:

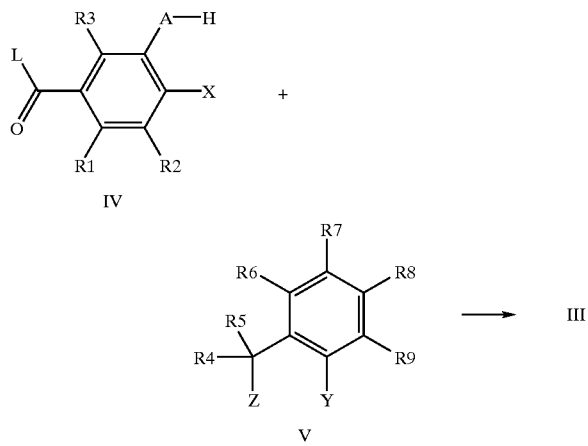

In this case, Z is a leaving group amenable to easy nucleophilic substitution, such as, for example, chlorine, bromine, iodine, mesylate, tosylate or trifluoromethanesulfonate. The derivatives IV and V are reacted in a suitable solvent such as DMF, THF or acetonitrile, using a base such as triethylamine or DIPEA, at a temperature between −20° C. and the boiling point of the solvent, preferably at a temperature of between 0° C. and 40° C.

The resulting compounds (within the scope of formula I) are substituted aroylguanidines, which are generally weak bases and are able to bind acid to form salts. Suitable acid addition salts are salts of all pharmacologically acceptable acids, for example halides, especially hydrochlorides, lactates, sulfates, citrates, tartrates, acetates, phosphates, methylsulfonates, p-toluenesulfonates.

Biological Properties and Medical Uses

Compared with known compounds, the compounds of the invention are distinguished by exceptionally high activity in inhibition of Na$^+$/H$^+$ exchange. Just like the known compounds, they have no undesired and disadvantageous salurific properties but have very good antiarrhythmic properties as are important, for example for the treatment of disorders occurring in association with manifestations of oxygen deficiency. As a consequence of their pharmacological properties, the compounds are outstandingly suitable as antiarrhythmic medicaments with a cardioprotective component for prophylaxis of infarction and treatment of infarction, and for the treatment of angina pectoris, and they also inhibit or greatly reduce in a preventive manner the pathophysiological processes associated with the development of ischemia-induced damage, especially in the initiation of ischemia-induced cardiac arrhythmias. Because of their protective effects against pathological hypoxic and ischemic situations, the compounds of the invention, of formula I, can be used, as a consequence of inhibition of the cellular Na$^+$/H$^+$ exchange mechanism, as medicaments for the treatment of all acute or chronic damage induced by ischemia or disorders induced primarily or secondarily thereby. This relates to their use as medicaments for surgical operations, e.g. in organ transplants, where the compounds can be used both to protect the organs in the donor before and during removal, to protect removed organs for example during treatment with or storage thereof in physiological bath fluids, and on transferring to the recipient organism. The compounds are likewise valuable medicaments with a protective effect when angioplastic surgical operations are performed for example on the heart and on peripheral vessels. In accordance with their protective effect against ischemia-induced damage, the compounds are also suitable as medicaments for the treatment of ischemias of the nervous system, especially of the CNS, being suitable, for example, for the treatment of stroke or cerebral edema. In addition, the compounds of the invention, of formula I, are likewise suitable for the treatment of types of shock such as, for example, of allergic, cardiogenic, hypovolemic and bacterial shock.

In addition, the compounds of the invention, of formula I, are distinguished by a strong inhibitory effect on the proliferation of cells, for example fibroblast cell proliferation and the proliferation of smooth vascular muscle cells. The compounds of formula I are therefore suitable as valuable therapeutic agents for disorders in which cell proliferation represents a primary or secondary cause, and can therefore be used as antiatherosclerotics, agents to prevent late complications of diabetes, cancers, fibrotic disorders such as pulmonary fibrosis, hepatic fibrosis or renal fibrosis, organ hypertrophies and hyperplasias, especially for prostate hyperplasia and prostate hypertrophy.

The compounds of the invention are effective inhibitors of the cellular sodium-proton antiporter (Na$^{30}$/H$^+$ exchanger)

which in numerous disorders (essential hypertension, atherosclerosis, diabetes etc.) is also increased in cells which are readily amenable to measurements, such as, for example, in erythrocytes, platelets or leukocytes. The compounds of the invention are therefore suitable as excellent and simple scientific tools, for example in their use as diagnostic aids for the determination and differentiation of particular forms of hypertension, but also of atherosclerosis, of diabetes, proliferative disorders etc. In addition, the compounds of formula I are suitable for preventive therapy to prevent the development of high blood pressure, for example of essential hypertension.

It has additionally been found that compounds of formula I show a beneficial effect on serum lipoproteins. It is generally acknowledged that blood lipid levels which are too high, so called hyperlipoproteinemias, represent a considerable risk factor for the development of arteriosclerotic vascular lesions, especially coronary heart disease. The lowering of elevated serum lipoproteins therefore has exceptional importance for the prophylaxis and regression of atherosclerotic lesions. Besides a reduction in total serum cholesterol, it is particularly important to reduce the proportion of specific atherogenic lipid fractions of this total cholesterol, especially the low density lipoproteins (LDL) and the very low density lipoproteins (VLDL), because these lipid fractions represent an atherogenic risk factor. By contrast, a protective function against coronary heart disease is ascribed to the high density lipoproteins. Accordingly, hypolipidemics should be able to reduce not only total cholesterol but, in particular, the VLDL and LDL serum cholesterol fractions. It has now been found that compounds of formula I show valuable therapeutically utilizable properties in relation to the effect on the serum lipid levels. Thus, they significantly reduce the elevated serum LDL and VLDL concentrations which are to be observed for example due to increased dietary intake of a cholesterol- and lipid-rich diet or in association with pathological metabolic changes, for example, genetically related hyperlipidemias. They can therefore be used for the prophylaxis and regression of atherosclerotic lesions through the elimination of a causal risk factor. These include not only primary hyperlipidemias but also certain secondary hyperlipidemias as occur, for example, in association with diabetes. In addition, the compounds of formula I lead to a marked reduction in the infarctions induced by metabolic abnormalities and, in particular, a significant reduction in the induced infarct size and its severity. Compounds of formula I further lead to effective protection against endothelial damage induced by metabolic abnormalities. This protection of vessels against the syndrome of endothelial dysfunction makes compounds of formula I valuable medicaments for the prevention and treatment of coronary vasospasms, of atherogenesis and of atherosclerosis, of left-ventricular hypertrophy and of dilated cardiomyopathy, and thrombotic disorders.

Said compounds are therefore advantageously used for producing a medicament for the treatment of hypercholesterolemia; for producing a medicament for the prevention of atherogenesis; for producing a medicament for the prevention and treatment of atherosclerosis, for producing a medicament for the prevention and treatment of disorders induced by elevated cholesterol levels, for producing a medicament for the prevention and treatment of disorders induced by endothelial dysfunction, for producing a medicament for the prevention and treatment of atherosclerosis-induced hypertension, for producing a medicament for the prevention and treatment of atherosclerosis-induced thromboses, for producing a medicament for the prevention and treatment of hypercholesterolemia—induced and endothelial dysfunction—induced ischemic damage and postischemic reperfusion damage, for producing a medicament for the prevention and treatment of hypercholesterolemia—induced and endothelial dysfunction—induced cardiac hypertrophies, cardiomyopaties and congestive heart failure (CHF), for producing a medicament for the prevention and treatment of hypercholesterolemia—induced and endothelial dysfunction—induced coronary vasospasms and myocardial infarctions, for producing a medicament for the treatment of said disorders in combinations with hypotensive substances, preferably with angiotensin converting enzyme (ACE) inhibitors and angiotensin receptor antagonists. A combination of an NHE inhibitor of formula I with a hypolipidemic active ingredient, preferably with an HMG-CoA reductase inhibitor (e.g. lovastatin or pravastatin), the latter having a hypolipidemic effect and thus increasing the hypolipidemic properties of the NHE inhibitor of formula I proves to be a favorable combination with enhanced effect and reduced active ingredient usage. The administration of sodium/proton exchange inhibitors of formula I as novel medicaments for reducing elevated blood lipid levels, and the combination of sodium/proton exchange inhibitors with hypotensive medicaments and/or medicaments having hypolipidemic activity are claimed.

Also claimed are the administration of sodium/proton exchange inhibitors of formula I, and the combination of sodium/proton exchange inhibitors with hypotensive medicaments, especially with ACE inhibitors (for example ramipril) and with angiotensin receptor antagonists (for example losartan) as novel medicaments for the treatment of CHF.

Medicaments comprising a compound I can moreover be administered orally, parenterally, intravenously, rectally or by inhalation, with the preferred administration being dependent on the particular appearance of the disorder. The compounds I can moreover be used alone or together with pharmaceutical excipients, both in veterinary medicine and in human medicine.

Excipients suitable for the desired pharmaceutical formulation are familiar to the skilled worker on the basis of his expert knowledge. Besides solvents, gel formers, suppository bases, tablet excipients and other active ingredient carriers, it is possible to use, for example, antioxidants, dispersants, emulsifiers, antifoams, masking flavors, preservatives, solubilizers or colors.

For a form for oral use, the active compounds are mixed with the additives suitable for this purpose, such as carriers, stabilizers or inert diluents, and converted by convenional methods into suitable dosage forms such as tablets, coated tablets, two-piece capsules, aqueous, alcoholic or oily solutions. Examples of inert carriers which can be used are gum arabic, magnesia, magnesium carbonate, potassium phosphate, lactose, glucose or starch, especially corn starch. Preparation can moreover take place both as dry and as wet granules. Examples of suitable oily carriers or solvents are vegetable or animal oils such as sunflower oil or fish liver oil.

For subcutaneous or intravenous administration, the active compounds are converted into a solution, suspension or emulsion, if desired with the substances customary for this purpose, such as solubilizers, emulsifiers or other excipients. Examples of suitable solvents are: water, physiological saline or alcohol, e.g. ethanol, propanol, glycerol, either as sugar solutions such as glucos or mannitol solutions, or else a mixture of the various solvents mentioned.

Suitable as pharmaceutical formulation for administration in the form of aerosols or sprays are, for example, solutions, suspensions or emulsions of the active ingredient of formula I in a pharmaceutically acceptable solvent such as, in particular, ethanol or water, or a mixture of such solvents. The formulation may if required also comprise other pharmaceutical excipients such as surfactants, emulsifiers and stabilizers, and a propellant gas. Such a preparation normally contains the active ingredient in a concentration of about 0.1 to 10, in particular of about 0.3 to 3% by weight.

The dosage of the active ingredient of formula I to be administered and the frequency of administration depend on the potency and duration of action of the compounds used; also on the nature and severity of the disorder to be treated, and on the sex, age, weight and individual response of the mammal to be treated.

On average, the daily dose of a compound of formula I for a patient weighing about 75 kg is at least 0.001 mg/kg, preferably 0.01 mg/kg, up to a maximum of 10 mg/kg, preferably up to a maximum of 1 mg/kg, of bodyweight. For acute episodes of the disorder, for example immediately after suffering a myocardial infarction, it may be necessary for the dosages also to be higher and, in particular, more frequent, e.g. up to 4 single doses per day. Especially on i.v. use, for example for an infarct patient in an intensive care unit, up to 200 mg per day and kg of bodyweight may be necessary.

| List of abbreviations: | |
|---|---|
| DIPEA | diisopropylethylamine |
| DMA | N,N-dimethylacetamide |
| DME | 1,2-dimethoxyethane |
| DMF | N,N-dimethylformamide |
| EA | ethyl acetate (EtOAc) |
| eq. | equivalent |
| MeOH | methanol |
| Pd(dppf)$_2$ | [1,1'-bis(diphenylphosphino)ferrocene]palladium(II) chloride/methylene chloride complex (1:1) |
| RT | room temperature |
| m.p. | melting point |
| THF | tetrahydrofuran |

DETAILED DESCRIPTION OF PARTICULAR EMBODIMENTS

General Method for the Synthesis of Dihydrothiaphenanthrenecarbonylguanidines

Stage 1) Methyl 4-bromo-5-chlorosulfonyl-2-methylbenzoate 12 g of 4-bromo-5-chlorosulfonyl-2-methylbenzoic acid (J.Med.Chem. 1997, 40, 2017) and 20 ml of thionyl chloride were boiled under reflux with exclusion of moisture for 8 hours. The excess thionyl chloride was removed in vacuo in a rotary evaporator, and the residue was taken up in about 50 ml of dry toluene and again evaporated. The crude acid chloride was dissolved in 25 ml of anhydrous toluene and, after addition of 1.7 ml of MeOH, stirred at 50° C. for 2 h. A further 1.7 ml of MeOH were then added, followed by stirring at 50° C. for 4 h. The reaction mixture was diluted with 200 ml of EA and washed with 100 ml of a saturated aqueous NaHCO$_3$ solution. After drying over Na$_2$SO$_4$, the solvents were removed in vacuo. 11.0 g of a pale yellow oil were obtained and were used without further purification.

Stage 2) 2-Bromo-5-methoxycarbonyl-4-methylbenzenesulfinic Acid 550 mg of Na$_2$SO$_3$ were dissolved in 2 ml of water and, at 70° C., a solution of 337 mg of methyl 4-bromo-5-chlorosulfonyl-2-methylbenzoate in 2 ml of DME was added dropwise. During the dropwise addition, the solution became weakly acidic (pH=5). The mixture was then stirred at 70° C. for 2.5 h, allowed to cool and adjusted to pH=1–2 with aqueous HCl solution. It was diluted with 50 ml of EA and washed with 50 ml of a saturated aqueous NaCl solution. After drying over Na$_2$SO$_4$, the solvents were removed in vacuo. 228 mg of a pale yellow oil were obtained and were used without further purification.

Stage 3) Methyl 4-bromo-5-(2-bromophenylmethanesulfonyl)-2-methylbenzoate 150 mg (0.51 mmol) of 2-bromo-5-methoxycarbonyl-4-methylbenzenesulfinic acid (stage 2) were dissolved in 1.5 ml of DMF. To this were added 128 mg (0.51 mmol) of 2-bromobenzyl bromide dissolved in 0.5 ml of DMF, and 0.1 ml (0.56 mMol) of DIPEA, and the mixture was stirred at room temperature with exclusion of moisture for 16 hours. The reaction solution was filtered, diluted with 20 ml of EA and washed with 20 ml of 1N hydrochloric acid and then 20 ml of 5% strength brine. The organic phase was forced through a drying cartridge (anhydrous sodium sulfate), and the cartridge was washed with 5 ml of EA. The filtrate was evaporated. The crude product was purified by preparative HPLC.

In accordance with the general reaction equation

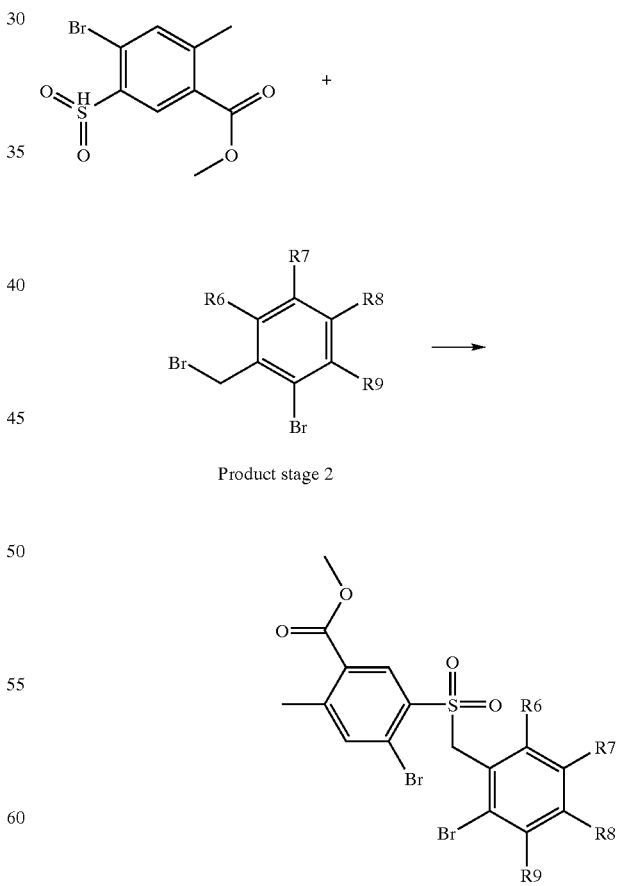

the following products were prepared analogously:

| No. | Benzyl bromide | Product |
|---|---|---|
| 2 | 1-Bromo-2-(bromomethyl)naphthalene | Methyl 4-bromo-5-(1-bromonaphthalen-2-ylmethanesulfonyl)-2-methylbenzoate |
| 3 | 2-Bromo-4-methylbenzyl bromide | Methyl 4-bromo-5-(2-bromo-4-methyl-phenylmethanesulfonyl)-2-methylbenzoate |
| 4 | 1-Bromo-2-bromomethyl-4-chlorobenzene | Methyl 4-bromo-5-(2-bromo-5-chloro-phenylmethanesulfonyl)-2-methylbenzoate |
| 5 | 2-Bromo-1-bromomethyl-4-fluorobenzene | Methyl 4-bromo-5-(2-bromo-4-fluoro-phenylmethanesulfonyl)-2-methylbenzoate |
| 6 | 1-Bromo-2-bromomethyl-3-fluorobenzene | Methyl 4-bromo-5-(2-bromo-6-fluoro-phenylmethanesulfonyl)-2-methylbenzoate |
| 7 | 2-Bromo-1-bromomethyl-4-chlorobenzene | Methyl 4-bromo-5-(2-bromo-4-chloro-phenylmethanesulfonyl)-2-methylbenzoate |
| 8 | 1-Bromo-2-bromomethyl-4-methoxybenzene | Methyl 4-bromo-5-(2-bromo-5-methoxy-phenylmethanesulfonyl)-2-methylbenzoate |
| 9 | 1-Bromo-2-bromomethyl-3-chlorobenzene | Methyl 4-bromo-5-(2-bromo-6-chloro-phenylmethanesulfonyl)-2-methylbenzoate |
| 10 | 2-Bromo-1-bromomethyl-3-methylbenzene | Methyl 4-bromo-5-(2-bromo-3-methyl-phenylmethanesulfonyl)-2-methylbenzoate |
| 11 | 1-Bromo-2-bromomethyl-4-methylbenzene | Methyl 4-bromo-5-(2-bromo-5-methyl-phenylmethanesulfonyl)-2-methylbenzoate |

Those benzyl bromides employed which could not be purchased were prepared either from the corresponding methyl aromatic compounds by free-radical bromination with N-bromosuccinimide or from the benzyl alcohols by reaction with aqueous HBr or methanesulfonyl chloride/triethylamine followed by tetrabutylammonium bromide.

The crude products were stirred with acetonitrile/water=9:1 (1 ml), possibly with the addition of 0.2 ml of DMF, filtered with suction through cartridges and washed with acetonitrile/water=9:1 (0.5 ml). The precipitated solids were dried in a vacuum oven at 50° C., and the purities were >80% according to HPLC/MS. The mother liquors were purified by preparative HPLC because they still contained a large proportion of product.

Stage 4) Methyl 6-methyl-9, 9-dioxo-9, 10-dihydro-9-thiaphenanthrene-7-carboxylate 68 mg (0.266 mmol) of bis(pinakolato)diboron, 71 mg (0.725 mmol) of potassium acetate and 9 mg (0.012 mmol) of Pd(dppf)$_2$ were introduced into 2 ml of DMA. To this were added 112 mg (0.242 mmol) of methyl 4-bromo-5-(2-bromophenylmethanesulfonyl)-2-methylbenzoate (stage 3) dissolved in 4 ml of DMA, and the mixture was stirred at 80° C. under protective gas overnight. The reaction solution was filtered through silica gel and washed with 20 ml of EA. The organic phase was washed with water and 5% strength brine, dried over anhydrous sodium sulfate and evaporated in vacuo. The crude product was purified by preparative HPLC.

In accordance with the general reaction equation

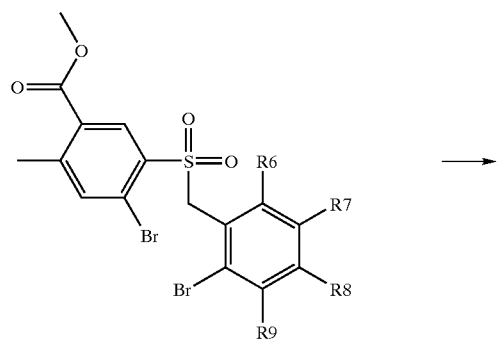

Product stage 3)

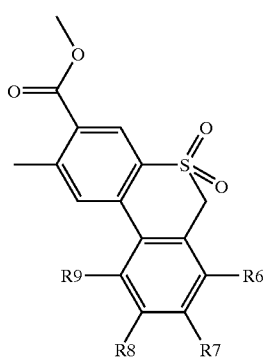

Product stage 4)

the following products were prepared analogously:

| No. | Product |
|---|---|
| 2 | Methyl 2-methyl-5,5-dioxo-5,6-dihydro-5-thiabenzo[c]phenanthrene-3-carboxylate |
| 3 | Methyl 3,6-dimethyl-9,9-dioxo-9,10-dihydro-9-thiaphenanthrene-7-carboxylate |
| 4 | Methyl 2-chloro-6-methyl-9,9-dioxo-9,10-dihydro-9-thiaphenanthrene-7-carboxylate |
| 5 | Methyl 3-fluoro-6-methyl-9,9-dioxo-9,10-dihydro-9-thiaphenanthrene-7-carboxylate |
| 6 | Methyl 1-fluoro-6-methyl-9,9-dioxo-9,10-dihydro-9-thiaphenanthrene-7-carboxylate |
| 7 | Methyl 3-chloro-6-methyl-9,9-dioxo-9,10-dihydro-9-thiaphenanthrene-7-carboxylate |
| 8 | Methyl 2-methoxy-6-methyl-9,9-dioxo-9,10-dihydro-9-thiaphenanthrene-7-carboxylate |
| 9 | Methyl 1-chloro-6-methyl-9,9-dioxo-9,10-dibydro-9-thiaphenanthrene-7-carboxylate |
| 10 | Methyl 4,6-dimethyl-9,9-dioxo-9,10-dihydro-9-thiaphenanthrene-7-carboxylate |
| 11 | Methyl 2,6-dimethyl-9,9-dioxo-9,10-dihydro-9-thiaphenanthrene-7-carboxylate |

Stage 5) Dihydrothiaphenanthrenecarbonylguanidines, General Method

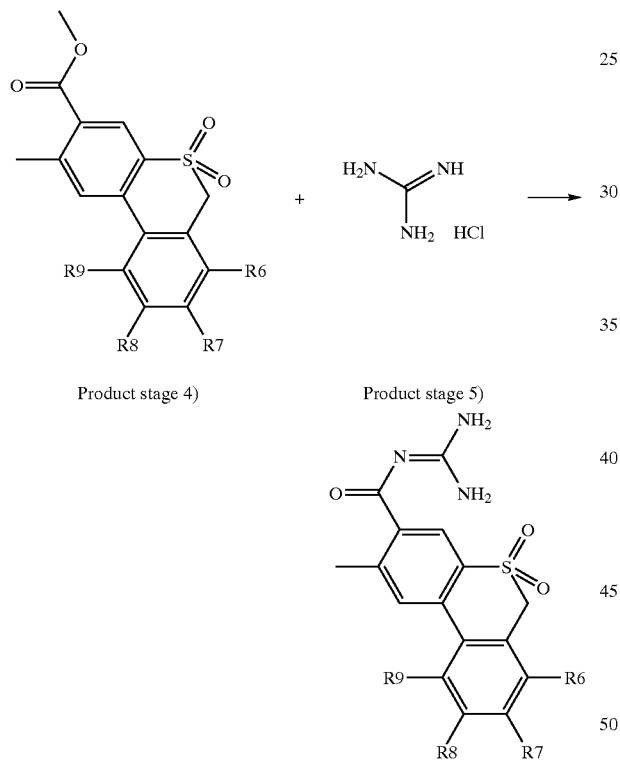

53 mg (0.5 mmol) of potassium tert.-butoxide were suspended in 2 ml of dry DMF. To this were added 50 mg (0.55 mmol) of guanidine hydrochloride, and the suspension was stirred at RT with exclusion of moisture for 30 min. Then 0.1 mmol of the methyl ester from stage 4 dissolved in 1 ml of DMF was added, and the mixture was stirred at RT overnight. The precipitated salts were filtered off, and the filtrate was immediately purified by preparative HPLC (column material Merck Supersphere RP1 8e, acetonitrile/water gradient with 0.1% formic acid as buffer). The resulting products were characterized by analytical HPLC/MS on an Agilent series 1100 system.

Mass detection was carried out with positive ionization.

Method A:

| | |
|---|---|
| Column: | MERCK LiChroCart 55-2 |
| Packing: | PuroSpher STAR RP18 |
| Flow rate: | 0.75 ml/min |
| Temperature: | 40° C. |
| Gradient: | |
| Solvent A | acetonitrile/water (90:10) + 0.5% formic acid |
| Solvent B | acetonitrile/water (10:90) + 0.5% formic acid |

| Time [min] | Solv. B [%] |
|---|---|
| 0.00 | 95.0 |
| 0.50 | 95.0 |
| 1.75 | 5.0 |
| 4.25 | 5.0 |
| 4.50 | 95.0 |
| 5.00 | 95.0 |
| 6.20 | STOP |

Method B:

| | |
|---|---|
| Column: | YMC J' Sphere ODS H80 |
| Packing: | 4µ |
| Flow rate: | 1.0 ml/min |
| Temperature: | 30° C. |
| Gradient: | |
| Solvent A | water + 0.05% trifluoroacetic acid |
| Solvent B | acetonitrile |

| Time [min] | Solv. B [%] |
|---|---|
| 0.00 | 10.0 |
| 2.50 | 95.0 |
| 3.30 | 95.0 |
| 3.35 | 10.0 |
| 3.60 | STOP |

The title compounds of examples 1–11 were synthesized by the general method of synthesizing dihydrothiaphenanthrenecarbonylguanidines:

EXAMPLE 1

N-(6-Methyl-9,9-dioxo-9,10-dihydro-9-thiaphenanthrene-7-carbonyl)guanidinium Formate

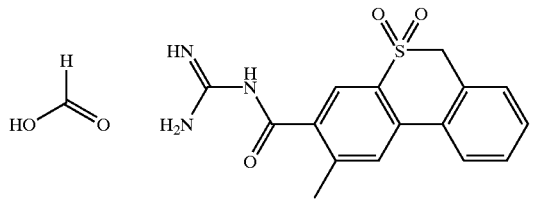

MS (ES): 330 (M+1)$^+$ retention time 2.384 min (220 nm, method A)

EXAMPLE 2

N-(2-Methyl-5,5-dioxo-5,6-dihydro-5-thiabenzo[c]phenanthrene-3-carbonyl)guanidinium Formate

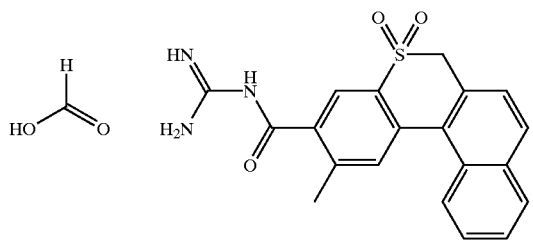

MS (ES): 380 (M+1)$^+$ retention time 1.793 min (220 nm, method B)

EXAMPLE 3

N-(3,6-Dimethyl-9,9-dioxo-9,10-dihydro-9-thiaphenanthrene-7-carbonyl)-guanidinium Formate

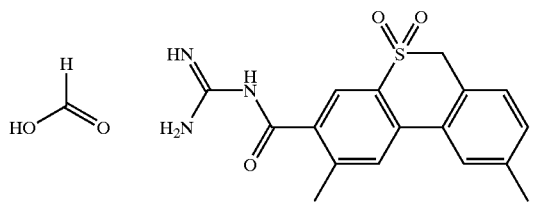

MS (ES): 344 (M+1)$^+$ retention time 2.411 min (220 nm, method A)

EXAMPLE 4

N-(2-Chloro-6-methyl-9,9-dioxo-9,10-dihydro-9-thiaphenanthrene-7-carbonyl)guanidinium Formate

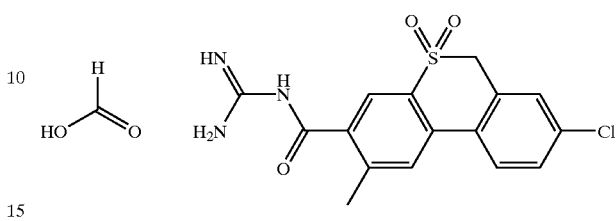

MS (ES): 364 (M+1)$^+$ retention time 2.390 min (220 nm, method A)

EXAMPLE 5

N-(3-Fluoro-6-methyl-9,9-dioxo-9,10-dihydro-9-thiaphenanthrene-7-carbonyl)guanidinium Formate

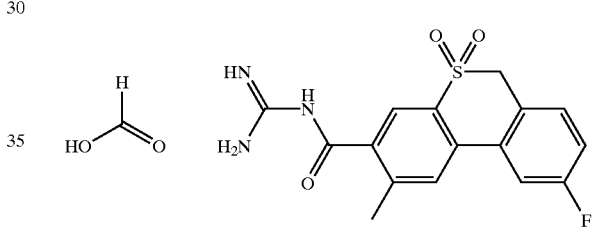

MS (ES): 348 (M+1)$^+$ retention time 2.215 min (220 nm, method A)

EXAMPLE 6

N-(1-Fluoro-6-methyl-9,9-dioxo-9,10-dihydro-9-thiaphenanthrene-7-carbonyl)guanidinium Formate

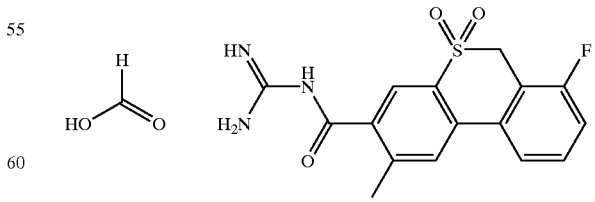

MS (ES): 348 (M+1)$^+$ retention time 2.218 min (220 nm, method A)

EXAMPLE 7

N-(3-Chloro-6-methyl-9,9-dioxo-9,10-dihydro-9-thiaphenanthrene-7-carbonyl)guanidinium Formate

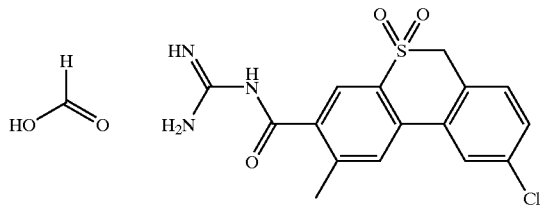

MS (ES): 364 (M+1)$^+$ retention time 2.394 min (220 nm, method A)

BEISPIEL 8

N-(2-Methoxy-6-methyl-9,9-dioxo-9,10-dihydro-9-thiaphenanthrene-7-carbonyl)guanidinium Formate

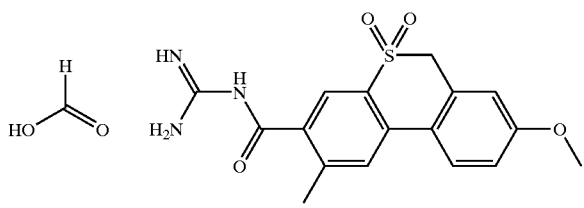

MS (ES): 360 (M+1)$^+$ retention time 2.271 min (220 nm, method A)

EXAMPLE 9

N-(1-Chloro-6-methyl-9,9-dioxo-9,10-dihydro-9-thiaphenanthrene-7-carbonyl)guanidinium Formate

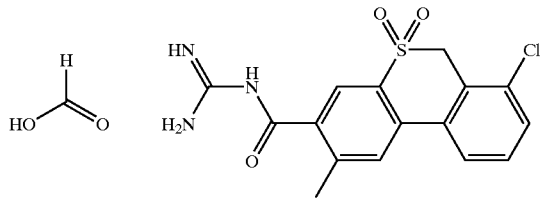

MS (ES): 364 (M+1)$^+$ retention time 2.358 min (220 nm, method A)

EXAMPLE 10

N-(4,6-Dimethyl-9,9-dioxo-9,10-dihydro-9-thiaphenanthrene-7-carbonyl)-guanidinium Formate

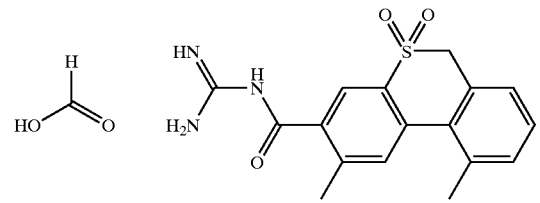

MS (ES): 344 (M+1)$^+$ retention time 2.302 min (220 nm, method A)

EXAMPLE 11

N-(2,6-Dimethyl-9,9-dioxo-9,10-dihydro-9-thiaphenanthrene-7-carbonyl)-guanidinium Formate

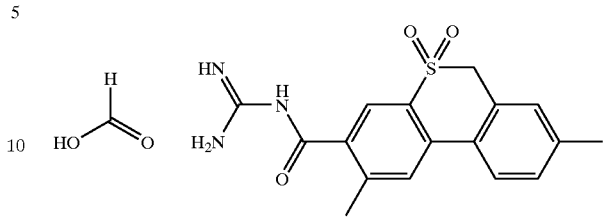

MS (ES): 344 (M+1)$^+$ retention time 2.671 min (220 nm, method A)

Jansen NHE Inhibition Method

The NHE-1 inhibition IC$_{50}$ [nM] was determined as follows:

FLIPR Assay for Determining NHE-1 Inhibitors by Measurement of the Recovery in pH$_i$ in Transfected Cell Lines Which Express Human NHE-1

The assay is carried out in an FLIPR (fluorometric imaging plate reader) with black-walled 96-well microtiter plates with clear bases. The transfected cell lines expressing the various NHE subtypes (the parental cell line LAP-1 [obtained from Prof. Pouysségur, Nice] shows no endogenous NHE activity as a result of mutagenesis and subsequent selection) are seeded the preceding day at a density of ~25 000 cells/well. [The growth medium for the transfected cells (Iscove +10% fetal calf serum) additionally contains G418 as selection antibiotic in order to ensure the presence of the transfected sequences.]

The actual assay starts with the removal of the growth medium and addition of 100 µl of loading buffer per well (5 µM BCECF-AM [2', 7'-bis(carboxyethyl)-5-(and-6)-carboxyfluorescein, acetoxymethyl ester] in 20 mM NH$_4$Cl, 115 mM choline chloride, 1 mM MgCl$_2$, 1 mM CaCl$_2$, 5 mM KCl, 20 mM HEPES, 5 mM glucose; pH 7.4 [adjusted with KOH]). The cells are then incubated at 37° C. for 20 minutes. This incubation leads to loading of the cells with the fluorescent dye whose fluorescence intensity depends on pHi, and with NH$_4$Cl which makes the cells slightly alkaline. [The nonfluorescent dye precursor BCECF-AM is, as ester, membrane-permeable. The actual dye BCECF is not membrane-permeable but is liberated inside cells by esterases.]

After this incubation for 20 minutes, the loading buffer which contains NH$_4$Cl and free BCECF-AM is removed by washing three times in a cell washer (Tecan Columbus) with in each case 400 µl of washing buffer (133.8 mM choline chloride, 4.7 mM KCl, 1.25 mM MgCl$_2$, 1.25 mM CaCl$_2$, 0.97 mM K$_2$HPO$_4$, 0.23 mM KH$_2$PO$_4$, 5 mM HEPES, 5 mM glucose; pH 7.4 [adjusted with KOH]). The residual volume remaining in the wells is 90 µl (50–125 µl possible). This washing step removes the free BCECF-AM and results, as a consequence of the removal of the external NH$_4$$^+$ ions, in intracellular acidification (~pH$_i$ 6.3–6.4). Since the equilibrium of intracellular NH$_4$$^+$ with NH$_3$ and H$^+$ is disturbed by the removal of the extracellular NH$_4$$^+$ and by the subsequent instantaneous passage of the NH$_3$ through the cell membrane, the washing process results in H$^+$ remaining inside the cells, which is the cause of the intracellular acidification. This may eventually lead to cell death if it persists long enough.

It is important at this point that the washing buffer is sodium-free (<1 mM) because extracellular sodium ions would lead to an instantaneous recovery of the pH$_i$ through the activity of the cloned NHE isoforms.

It is likewise important for all the buffers used (loading buffer, washing buffer, recovery buffer) not to contain any HCO$_3^-$ ions, because the presence of bicarbonate would lead to activation of interfering bicarbonate-dependent pH$_i$ regulatory systems present in the parental LAP-1 cell line.

The microtiter plates with the acidified cells are then (up to 20 minutes after the acidification) transferred to the FLIPR. In the FLIPR, the intracellular fluorescent dye is excited by light with a wavelength of 488 nm generated by an argon laser, and the measured parameters (laser power, illumination time and aperture of the CCD camera incorporated in the FLIPR) are chosen so that the average fluorescence signal per well is between 30 000 and 35 000 relative fluorescence units.

The actual measurement in the FLIPR starts with a photograph being taken by the CCD camera every two seconds under software control. After ten seconds, the recovery of the intracellular pH is initiated by adding 90 µl of recovery buffer (133.8 mM NaCl, 4.7 mM KCl, 1.25 mM MgCl$_2$, 1.25 mM CaCl$_2$, 0.97 mM K$_2$HPO$_4$, 0.23 mM KH$_2$PO$_4$, 10 mM HEPES, 5 mM glucose; pH 7.4 [adjusted with NaOH]) by means of the 96-well pipettor incorporated in the FLIPR.

Positive control wells (100% NHE activity) are those to which pure recovery buffer is added, while negative controls (0% NHE activity) receive washing buffer. Recovery buffer with twice the concentration of test substance is added to all the other wells. Measurement in the FLIPR terminates after 60 measurements (two minutes).

The raw data are exported into the Activity Base program. This program firstly calculates the NHE activities for each tested substance concentration and, from these, the IC$_{50}$ values for the substances. Since the progress of PH$_i$ recovery is not linear throughout the experiment, but falls at the end owing to decreasing NHE activity at higher pH$_i$ values, it is important to select for evaluation of the measurement the part in which the increase in fluorescence of the positive controls is linear.

| Example | NHE-1 inhibition IC$_{50}$ [nM] |
|---|---|
| 1 | 15.6 |
| 2 | 24.2 |
| 3 | 8.6 |
| 4 | 10.8 |
| 5 | 15.6 |
| 6 | 16.5 |
| 7 | 11.7 |
| 8 | 10.2 |
| 9 | 13.9 |
| 10 | 67.7 |
| 11 | 19.5 |

While there have been described and pointed out fundamental novel features of the invention as applied to a preferred embodiment thereof, it will be understood that various omissions and substitutions and changes, in the form and details of the embodiments illustrated, may be made by those skilled in the art without departing from the spirit of the invention. The invention is not limited by the embodiments described above which are presented as examples only but can be modified in various ways within the scope of protection defined by the appended patent claims.

We claim:

1. A dihydrothiaphenanthrenecarbonylguanidine compound of formula I or a pharmaceutically suitable salt of said compound:

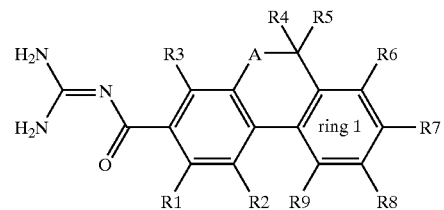

wherein:

R1 and R3 are independently selected from the group consisting of hydrogen, —(C1–C4)-alkyl, —(C1–C4)-alkoxy, —F, —Cl, —Br, —I, —CN, —NR10R11, —O$_p$—(CH$_2$)$_n$—(CF$_2$)$_x$—CF$_3$, and —(SO$_m$)$_p$—(CH$_2$)$_n$—(CF$_2$)$_x$—CF$_3$, wherein:

R10 and R11 are independently selected from the group consisting of hydrogen, —(C1–C4)-alkyl and —(CH$_2$)$_n$—(CF$_2$)$_x$—CF$_3$, m=0, 1 or 2, n=0, 1, 2, 3, 4, 5 or 6, x=0 or 1, and p=0 or 1;

R2 is selected from the group consisting of hydrogen, —F, —Cl, —Br, —I, —CN, —(C1–C4)-alkyl, methoxy, and —(C3–C8)-cycloalkyl;

R4 and R5 are independently selected from the group consisting of hydrogen and —(C1–C4) alkyl;

R6, R7, R8 and R9 are independently selected from the group consisting of hydrogen, —(C1–C4)-alkyl; —(C1–C4)-alkoxy, —F, —Cl, —Br, —I, —CN, —NR12R13, —O$_q$—(CH$_2$)$_r$—(CF$_2$)$_s$—CF$_3$ and —(SO$_w$)$_t$—(CH$_2$)$_u$—(CF$_2$)$_v$—CF$_3$, wherein:

R12 and R13 are independently selected from the group consisting of hydrogen and —(C1–C4)-alkyl, w=0, 1 or 2, r=0, 1, 2, 3, 4, 5, or 6, u=0, 1, 2, 3, 4, 5, or 6, q=0 or 1 s=0 or 1 t=0 or 1, and v=0 or 1; or

R6 and R7, together with ring 1, form a naphthalene system and R8 and R9 remain as defined above; or R7 and R8, together with ring 1, form a naphthalene system and R6 and R9 remain as defined above; or R8 and R9, together with ring 1, form a naphthalene system and R6 and R7 remain as defined above; and A is selected from the group consisting of —S—, —SO— and —SO$_2$—.

2. A compound of claim 1 or a pharmaceutically suitable salt of said compound, wherein:

R1 and R3 are independently selected from the group consisting of hydrogen, methyl, ethyl, methoxy, ethoxy, —F, —Cl, —CN, —NR10R11, —O$_p$—(CH$_2$)$_n$—CF$_3$ and —(SO$_m$)$_p$—(CH$_2$)$_n$—CF$_3$, wherein:

R10 and R11 are independently selected from the group consisting of hydrogen, methyl, ethyl and —CH$_2$—CF$_3$, m=0, 1 or 2, n=0, 1, 2 or 3, and p=0 or 1;

R2 is selected from the group consisting of hydrogen, —F, —Cl, —CN, —(C1–C4)-alkyl, methoxy, and —(C3–C6)-cycloalkyl;

R4 and R5 are independently selected from the group consisting of hydrogen, methyl and ethyl;

R6, R7, R8 and R9 are independently selected from the group consisting of hydrogen, —(C1–C4)-alkyl, methoxy, ethoxy, —F, —Cl, —CN, —NR12R13, —$O_q$—$(CH_2)_r$—$CF_3$ and —$(SO_w)_t$—$(CH_2)_u$—$CF_3$, wherein:

R12 and R13 are independently selected from the group consisting of hydrogen, methyl and ethyl,
w=0, 1 or 2;
r=0, 1, 2, or 3,
u=0, 1, 2, or 3,
q=0 or 1, and
t=0 or 1; or R6 and R7, together with ring 1, form a naphthalene system and R8 and R9 remain as defined in the preceding section of this claim; or R7 and R8, together with ring 1, form a naphthalene system and R6 and R9 remain as defined in the preceding section of this claim; or R8 and R9, together with ring 1, form a naphthalene system and R6 and R7 remain as defined in the preceding section of this claim; and A is selected from the group consisting of —S—, —SO— and —$SO_2$—.

3. A compound of claim 1 or and a pharmaceutically suitable salt of said compound, wherein:

R1 is selected from the group consisting of hydrogen, methyl, ethyl, methoxy, ethoxy, —F, —Cl, —NR10R11, —$O_p$—$(CH_2)_n$—$CF_3$ and —$(SO_m)_p$—$(CH_2)_n$—$CF_3$, wherein R10 and R11 are independently selected from the group consisting of hydrogen, methyl, ethyl and —$CH_2$—$CF_3$, m=0, 1 or 2, n=0 or 1, p=0 or 1;

R2 is selected from the group consisting of hydrogen, —F, —Cl, methyl, and —(C3–C6)-cycloalkyl;

R3, R4 and R5 are hydrogen;

R6, R7, R8 and R9 are independently selected from the group consisting of hydrogen, methyl, methoxy, ethoxy, —F, —Cl, —NR(12)R(13), —$O_q$—$(CH_2)_r$—$CF_3$ and —$(SO_w)_t$—$(CH_2)_u$—$CF_3$, wherein R12 and R13 are independently selected from the group consisting of hydrogen, methyl or ethyl; w=0, 1 or 2; q, r, t and u are independently zero or one; or R6 and R7, together with ring 1, form a naphthalene system and R8 and R9 remain as defined in the preceding section of this claim; or R7 and R8, together with ring 1, form a naphthalene system and R6 and R9 remain as defined in the preceding section of this claim; or R8 and R9, together with ring 1, form a naphthalene system and R6 and R7 remain as defined in the preceding section of this claim; and A is selected from the group consisting of —S—, —SO— and —$SO_2$—.

4. A compound of claim 1 or a pharmaceutically suitable salt of said compound, wherein:

R1 is selected from the group consisting of hydrogen, methyl, methoxy, ethoxy, —Cl, —NR10R11, —O—$CH_2$—$CF_3$ and —$(SO_m)_p$—$(CH_2)_n$—$CF_3$, wherein R(10) and R(11) are independently selected from the group consisting hydrogen, methyl, ethyl and —$CH_2$—$CF_3$; m is 0, 1 or 2; p is 0 or 1;

R2 is selected from the group consisting of hydrogen, —F, —Cl and methyl;

R3, R4 and R5 are hydrogen;

R6, R7, R8 and R9 are independently selected from the group consisting of hydrogen, methyl; methoxy, ethoxy, —F, —Cl, —O—$CH_2$—$CF_3$ and —$(SO_w)_t$—$(CH_2)_u$—$CF_3$, wherein w is 0, 1 or 2; t and u are independently zero or one; or R6 and R7, together with ring 1, form a naphthalene system and R8 and R9 remain as defined in the preceding section of this claim; or R7 and R8, together with ring 1, form a naphthalene system and R6 and R9 remain as defined in the preceding section of this claim; or R8 and R9, together with ring 1, form a naphthalene system and R6 and R7 remain as defined in the preceding section of this claim; and A is —$SO_2$—.

5. A pharmaceutical composition comprising an effective amount of a compound or a salt of a compounds of claim 1 and a suitable and physiologically tolerated carrier substance.

6. A method for treatment and prophylaxis of a disorder caused by ischemic states, comprising administering an effective amount of a compound or a salt of a compound of claim 1 in a suitable dosage form.

7. A method of claim 6, wherein said disorder is myocardial infarction or arrhythmias.

8. A method of claim 6, wherein said disorder is angina pectoris.

9. A method of claim 6, wherein said disorder is ischemic states of the heart.

10. A method of claim 6, wherein said disorder is ischemic states of the peripheral and central nervous system or stroke.

11. A method of claim 6, wherein said disorder is ischemic states of the peripheral organs and limbs.

12. A method of claim 6, wherein said disorder is a state of shock.

13. A pharmaceutical composition of claim 5, useful during surgical operations or organ transplantations.

14. A pharmaceutical composition of claim 5, useful for preservation and storage of transplants for surgical procedures.

15. A pharmaceutical composition of claim 5, useful for treatment of disorders in which cell proliferation represents a primary or secondary cause.

16. A pharmaceutical composition of claim 5, useful for treatment or prophylaxis of disorders of lipid metabolism.

* * * * *